United States Patent
Yokoi (10) Patent No.: US 11,163,074 B2
(45) Date of Patent: Nov. 2, 2021

(54) RADIATION IMAGING APPARATUS, AND CALIBRATION METHOD FOR PHOTON COUNTING TYPE DETECTOR

(71) Applicant: Hitachi, Ltd., Tokyo (JP)

(72) Inventor: Kazuma Yokoi, Tokyo (JP)

(73) Assignee: HITACHI, LTD., Tokyo (JP)

(*) Notice: Subject to any disclaimer, the term of this patent is extended or adjusted under 35 U.S.C. 154(b) by 0 days.

(21) Appl. No.: 16/768,708

(22) PCT Filed: Jan. 8, 2019

(86) PCT No.: PCT/JP2019/000236
§ 371 (c)(1),
(2) Date: Jun. 1, 2020

(87) PCT Pub. No.: WO2019/167429
PCT Pub. Date: Sep. 6, 2019

(65) Prior Publication Data
US 2020/0301031 A1    Sep. 24, 2020

(30) Foreign Application Priority Data

Mar. 2, 2018  (JP) .............................. JP2018-037330

(51) Int. Cl.
*A61B 6/03*    (2006.01)
*G01T 1/17*    (2006.01)
(Continued)

(52) U.S. Cl.
CPC .............. *G01T 1/2992* (2013.01); *A61B 6/03* (2013.01); *G01T 1/17* (2013.01); *G01T 7/005* (2013.01)

(58) Field of Classification Search
CPC ........... A61B 6/03; G01T 1/17; G01T 1/2992; G01T 7/005
See application file for complete search history.

(56) References Cited

U.S. PATENT DOCUMENTS

2011/0012014 A1*  1/2011  Livne ................... A61B 6/4042
                                              250/252.1
2014/0299757 A1* 10/2014  Akers ..................... G01T 1/167
                                              250/269.1
2016/0374629 A1   12/2016  Kawata et al.

FOREIGN PATENT DOCUMENTS

JP         2015-184116 A      10/2015

OTHER PUBLICATIONS

International Search Report of PCT/JP2019/000236 dated Mar. 19, 2019.

* cited by examiner

*Primary Examiner* — Mark R Gaworecki
(74) *Attorney, Agent, or Firm* — Mattingly & Malur, PC (57) ABSTRACT

A radiation imaging apparatus provided with a photon counting type detector for outputting an electric signal corresponding to energy of an incident radiation photon includes a measured value recording unit for measuring an attenuation value in the presence of a known calibration member while changing a threshold value of a detector output of the photon counting type detector and recording a measured value of the attenuation value for each threshold value of the detector output, a theoretical value calculation unit for calculating a theoretical value of the attenuation value in the presence of the calibration member with respect to multiple energies, a calibration information acquisition unit for acquiring a relation between the threshold value and the energy as calibration information by performing collation between the measured value and the theoretical value, and a calibration processing unit for converting the electric signal outputted from the photon counting type detector into energy.

6 Claims, 5 Drawing Sheets

(51) Int. Cl.
*G01T 7/00* (2006.01)
*G01T 1/29* (2006.01)

RADIATION IMAGING APPARATUS, AND CALIBRATION METHOD FOR PHOTON COUNTING TYPE DETECTOR

TECHNICAL FIELD

The present invention relates to a radiation imaging apparatus provided with a photon counting type detector, and to a calibration method for the photon counting type detector.

BACKGROUND ART

The development of a PCCT (Computed Tomography) apparatus provided with the photon counting type detector as the detector of photon counting type has been in progress. Since the photon counting type detector is capable of measuring energy of the radiation photon incident on the detector, the PCCT apparatus ensures to provide a medical image that contains more information than in the case of using a generally employed CT apparatus, for example, the medical image divided into a plurality of energy components.

In order to allow the photon counting type detector to measure energy of the radiation photon, it is necessary to calibrate a relation between an output wave peak (detector output) of the photon counting type detector and energy (incident energy) of the radiation photon incident on the photon counting type detector. Since the calibration is carried out after an elapse of a predetermined period from the product shipment and the product delivery, it is preferable to carry out simple and quick calibration.

In PTL 1, the simple and quick calibration may be carried out using a linear equation obtained by the most frequent value of the detector output acquired by measuring the X-ray irradiated from the X-ray tube constituted by a certain target material by means of the photon counting type detector, and a peak value of the target material property around the characteristic X-ray.

CITATION LIST

Patent Literature

PTL 1: Japanese Patent Application Laid-Open No. 2015-184116

SUMMARY OF INVENTION

Technical Problem

PTL 1 ensures the simple and quick calibration. However, since the linear relation between the detector output and the incident energy is prerequisite, the non-linear relation therebetween, if any, may deteriorate the calibration accuracy.

It is an object of the present invention to provide a radiation imaging apparatus which allows improvement in the calibration accuracy of the photon counting type detector while ensuring the simple and quick calibration, and a calibration method for a photon counting type detector.

Solution to Problem

In order to accomplish the object, the present invention provides a radiation imaging apparatus provided with a photon counting type detector for outputting an electric signal corresponding to energy of an incident radiation photon. The apparatus includes a measured value recording unit for measuring an attenuation value in the presence of a known calibration member while changing a threshold value of a detector output of the photon counting type detector and recording a measured value of the attenuation value for each threshold value of the detector output, a theoretical value calculation unit for calculating a theoretical value of the attenuation value in the presence of the calibration member with respect to multiple energies, a calibration information acquisition unit for acquiring a relation between the threshold value and the energy as calibration information by performing collation between the measured value and the theoretical value, and a calibration processing unit for converting the electric signal outputted from the photon counting type detector into energy based on the calibration information.

The present invention provides a calibration method for a photon counting type detector for outputting an electric signal corresponding to energy of an incident radiation photon. The calibration method includes a measured value recording step of measuring an attenuation value in the presence of a known calibration member while changing a threshold value of a detector output of the photon counting type detector and recording a measured value of the attenuation value for each threshold value of the detector output, a theoretical value calculation step of calculating a theoretical value of the attenuation value in the presence of the calibration member with respect to multiple energies, and a calibration information acquisition step of acquiring a relation between the threshold value and the energy as calibration information by performing collation between the measured value and the theoretical value.

Advantageous Effects of Invention

The present invention provides the radiation imaging apparatus which allows improvement in the calibration accuracy of the photon counting type detector while ensuring the simple and quick calibration, and the calibration method for a photon counting type detector.

DESCRIPTION OF EMBODIMENT

An embodiment of the present invention will be described referring to the drawings. The radiation imaging apparatus according to the present invention is applied to the apparatus provided with the radiation source and the photon counting type detector. An explanation will be made, taking the X-ray as the radiation, and the X-ray CT apparatus as the radiation imaging apparatus.

EXAMPLE 1

Figure 1:
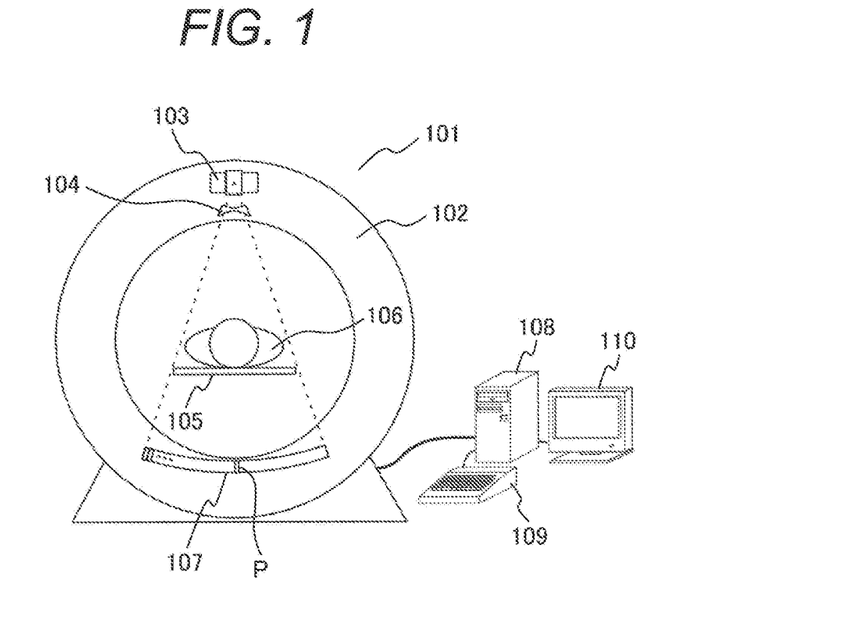
FIG. 1 is a view showing an overall structure of an X-ray CT apparatus 101 according to Example 1.

FIG. 1 is a view showing an overall structure of the X-ray CT apparatus 101 according to an example. The X-ray CT apparatus 101 includes a gantry 102, an X-ray tube 103, a bow tie filter 104, a bed 105, a detector panel 107, an arithmetic unit 108, an input unit 109, and a display unit 110. The X-ray radiated from the X-ray tube 103 is formed into a beam shape adapted to the size of a subject examinee 106. The X-ray is then irradiated to permeate through the subject examinee 106, and then detected by the detector panel 107. The X-ray tube 103 and the detector panel 107 are attached to the gantry 102 to face with each other while interposing the subject examinee 106, and revolve therearound as the gantry 102 is driven to rotate. As the gantry 102 is driven to rotate, the X-ray is irradiated from the X-ray tube 103, and measured by the detector panel 107 repeatedly so that projection data is acquired at various projection angles. As an image reconstruction processing is applied to the acquired projection data by the arithmetic unit 108, a tomographic image of the subject examinee 106 is generated, and displayed on the display unit 110. Upon acquisition of the projection data in relative movement between the bed 105 on which the subject examinee 106 lies and the gantry 102 to the direction of the body axis of the subject examinee 106, a volume image of the subject examinee 106 is generated. The dose of X-ray irradiated from the X-ray tube 103, the rotation speed of the gantry 102, and the relative movement speed between the gantry 102 and the bed 105 are set based on scan conditions inputted by an operator via the input unit 109. The arithmetic unit 108 is a hardware structure like the generally employed computer device, and includes a CPU (Central Processing Unit), a memory, an HDD (Hard Disk Drive), and the like for executing the correction processing of the projection data and the like, and controlling the respective components.

The detector panel 107 is constituted by a plurality of detector pixels P in an arc-like arrangement having an X-ray focus of the X-ray tube 103 as the center. The detector pixel P is a photon counting type detector which measures energy (incident energy) of the incident X-ray photon for generating an output in accordance with the incident energy.

Figure 2:
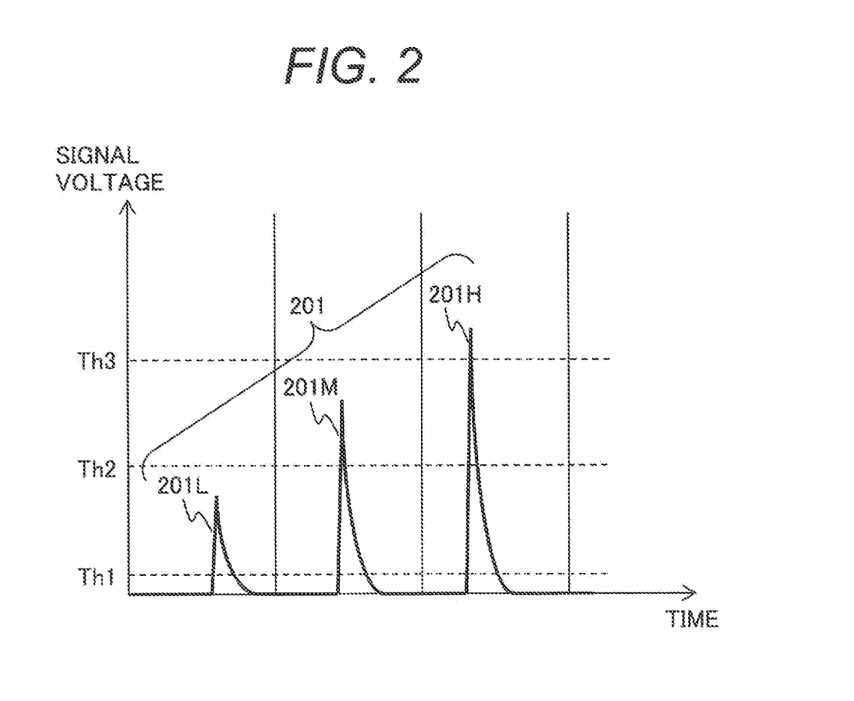
FIG. 2 is a view showing an example of an output waveform of a photon counting type detector.

An example of the output waveform of the photon counting type detector will be described referring to FIG. 2. An x-axis and a y-axis of FIG. 2 denote time and a signal voltage of the photon counting type detector, respectively. Upon every incidence of the X-ray photon, the photon counting type detector generates a pulse output 201. The peak value of the pulse output 201 becomes the value in accordance with the incident energy. FIG. 2 shows the pulse outputs 201 generated upon incidence of three kinds of X-ray photons each with different incident energy. The pulse output 201L indicates the incidence of the X-ray photon with low incident energy. The pulse output 201M indicates the incidence of the X-ray photon with medium incident energy. The pulse output 201H indicates the incidence of the X-ray photon with high incident energy. It is possible to decompose the incident X-ray photon into N kinds of energy in reference to a predetermined threshold value of the detector output from the photon counting type detector based on a relation between the detector output (detected peak) and the incident energy. Referring to FIG. 2, the incident X-ray photons are decomposed in reference to three threshold values Th1 to Th3 to three kinds of energy ranges, that is, the ranges from Th1 to Th2, from Th2 to Th3, and from Th3 onward. The decomposed energy range may be referred to as a bin.

As each of the detector pixels P has an individual energy characteristic (relation between the detector output and the incident energy) owing to resistance of the circuit element and unevenness in the capacitance, the detector output may differ in spite of the X-ray photon with the same incident energy. Accordingly, the relation between the detector output and the incident energy has to be calibrated for each of the detector pixels P.

Figure 3:
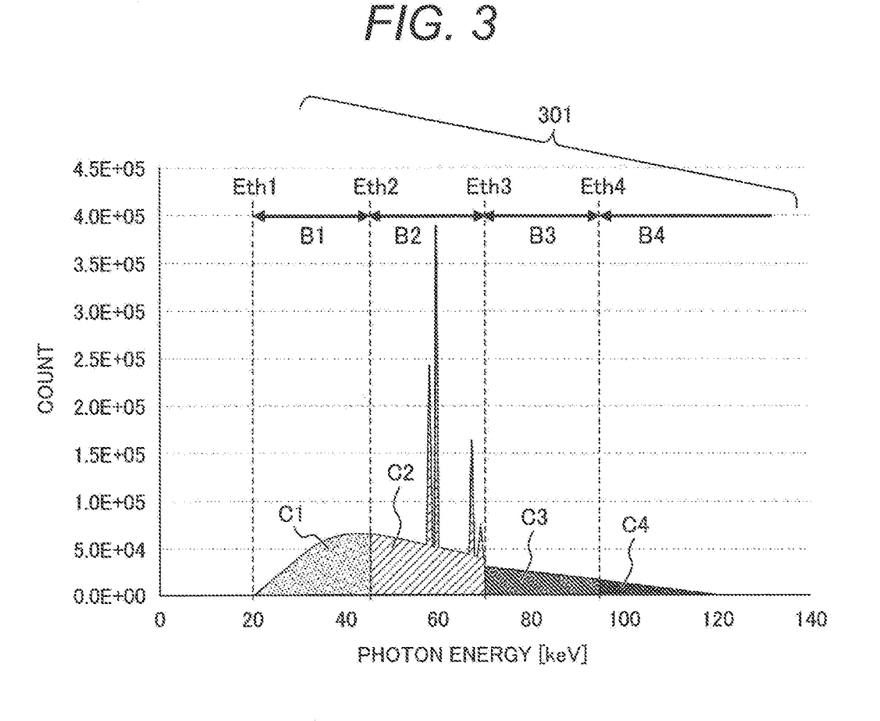
FIG. 3 is an explanatory view of energy decomposition.

Referring to FIG. 3, energy decomposition will be further described. An x-axis and a y-axis of FIG. 3 denote energy of the X-ray photon, and the number of the X-ray photons to be counted by the photon counting type detector, respectively. In order to decompose the X-ray energy exhibiting an energy spectrum 301 by the photon counting type detector, the energy is divided in reference to the predetermined threshold values of Eth1 to Eth4, for example. Specifically, as FIG. 3 shows, the X-ray photon energy is divided into a bin B1 from Eth1 to Eth2, a bin B2 from Eth2 to Eth3, a bin B3 from Eth3 to Eth4, and a bin B4 from Eth4 and onward. The X-ray photons of the respective bins will be counted. As FIG. 3 shows, the count numbers of the bins B1, B2, B3, and B4 are designated as C1, C2, C3, and C4, respectively. The accurate counting of the X-ray photons of the respective bins require further accurate correspondence relation between the threshold value of the detector output and the threshold value of the incident energy. Especially, calibration of the non-linear relation between the detector output and the incident energy using the linear equation may deteriorate the calibration accuracy.

Figure 4:
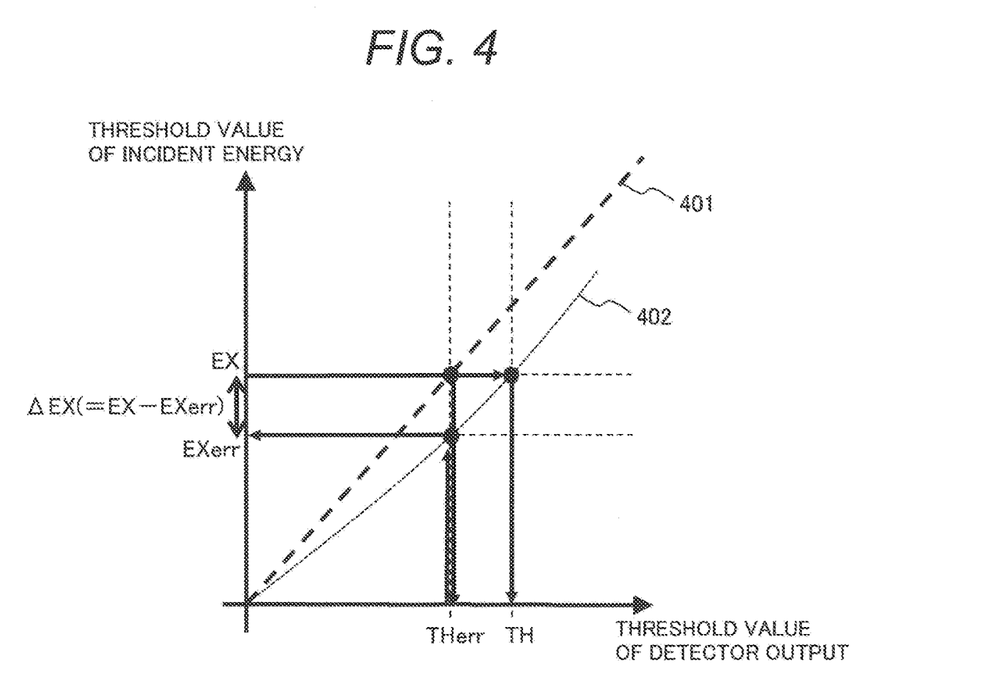
FIG. 4 is a view showing a relation between a threshold value of incident energy and a threshold value of a detector output.

Referring to FIG. 4, an explanation will be made on deterioration in calibration accuracy as a result of using the linear equation. An x-axis and a y-axis of FIG. 4 denote the threshold value of the detector output, and the threshold value of the incident energy, respectively. FIG. 4 shows an energy characteristic 401 expressed by the linear equation, and a non-linear energy characteristic 402 of the detector pixel P. As FIG. 4 shows, assuming that the threshold value of the incident energy is set to EX, TH is expected to be corresponded as the threshold value of the detector output of the detector pixel P. However, the use of the linear energy characteristic 401 sets the threshold value of the detector output to THerr. In the case of corresponding the THerr to the energy characteristic 402 of the detector pixel P, the threshold value of the incident energy becomes EXerr, resulting in an error $\Delta EX(=EX-EXerr)$. In the example, the energy characteristic 402 of the detector pixel P is not directly handled but acquired indirectly. That is, the measurement result of an attenuation value in the presence of the known calibration member while changing the threshold value of the detector output is collated with the theoretical value calculated with respect to multiple energy values so that the relation of the detector output with the energy characteristic 402 of the detector pixel P, that is, the incident energy, is calculated.

Essential parts of the example will be described referring to FIG. 5. Those essential parts may be constituted by a dedicated hardware, or by the software running on the arithmetic unit 108. The following explanation will be made by taking the essential parts of the example constituted by the software as an example. In the example, a measured value recording unit 451, a theoretical value calculation unit 452, a calibration information acquisition unit 453, and a calibration processing unit 454 are provided. Each of those units will be described hereinafter.

The measured value recording unit 451 measures the attenuation value in the presence of the calibration member while changing the threshold value of the detector output of the photon counting type detector of the detector panel 107, and records the measured value of the attenuation value for each threshold value of the detector output. The attenuation value represents the value expressing the intensity that attenuates the radiation, for example, X-ray to be absorbed or scattered in the substance such as the calibration member. The measured value Am of the attenuation value is obtained by the following formula using a count number CO of the X-ray photon in the absence of the calibration member, and a count number C of the X-ray photon in the presence of the calibration member.

$$Am = -\ln(C/CO) \quad \text{(formula 1)}$$

The attenuation value, that is, the count number of the X-ray photon is measured while changing the threshold value of the detector output. As the Am, C, and CO become functions of a threshold value S, the (formula 1) is rewritten to the following formula.

$$Am(S) = -\ln\{C(S)/CO(S)\} \quad \text{(formula 2)}$$

Figure 6:
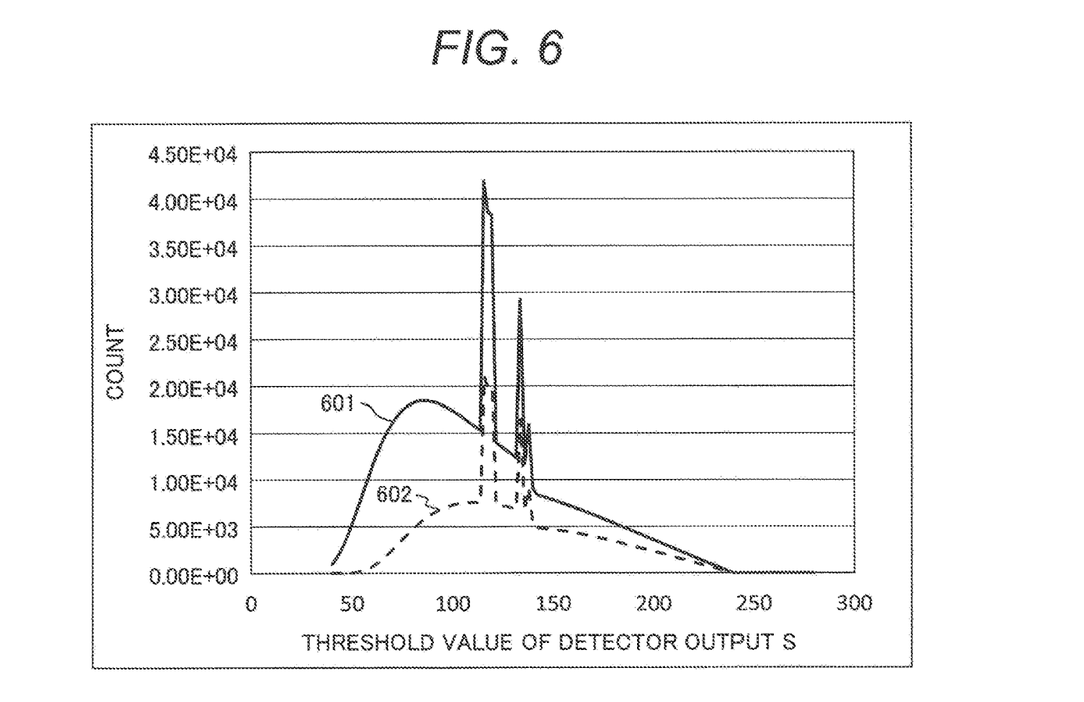
FIG. 6 is a view showing an example as a result of counting an X-ray photon while changing the threshold value of the detector output.

FIG. 6 shows an example of the result from counting the X-ray photon while changing the threshold value of the detector output. An x-axis and a y-axis of FIG. 6 denote the threshold value of the detector output, and the count number of the X-ray photon, respectively. Referring to FIG. 6, the solid line represents a count number 601 of the X-ray photon in the absence of the calibration member, and the dotted line represents a count number 602 of the X-ray photon in the presence of the calibration member. The measured value of the attenuation value exists in a range interposed between the solid line and the dotted line.

Figure 7:
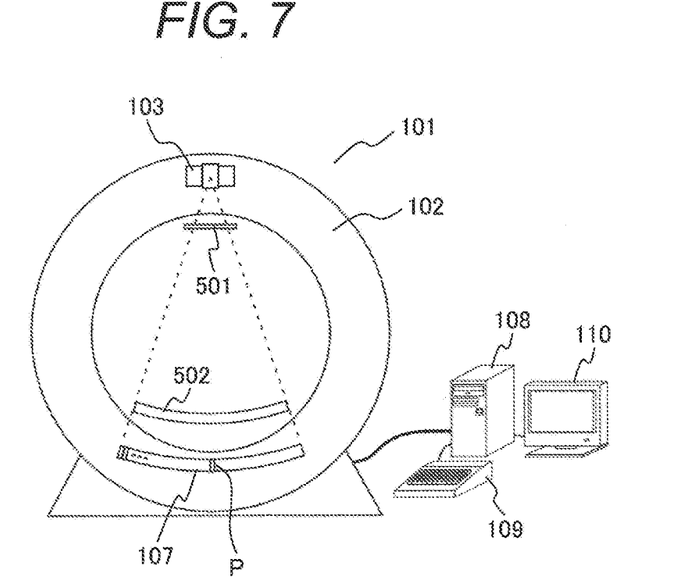
FIG. 7 is a view showing an exemplary arrangement of calibration members.

The material with known properties (atomic number composition, density) and known shape, for example, a tungsten flat plate, and an arc shaped molybdenum member may be used for forming the calibration member, and arranged as shown in FIG. 7. FIG. 7 shows an example that a flat plate type calibration member 501 and an arc type calibration member 502 are arranged in the X-ray CT apparatus 101. The flat plate type calibration member 501 is a calibration member with a flat shape and a uniform thickness which is easily manufactured and arranged. The arc type calibration member 502 is formed into the shape with a uniform length over a path from an X-ray focus of the X-ray tube 103 to each of the detector pixels P. The calibration member may be formed into the shape in accordance with the detector panel 107 with polygonal shape rather than the arc shape. At least one of the flat plate type calibration member 501 and the arc type calibration member 502 may be disposed in the X-ray CT apparatus 101. Preferably, the bow tie filter 104 and the bed 105 are removed in order to straighten radiation quality of the X-ray incident on the respective detector pixels P.

In order to measure the attenuation value for each threshold value of the detector outputs, two threshold values are set to count the X-ray photons in the range interposed between the two set threshold values. Ideally, the width between the threshold values is as narrow as possible. Assuming that the width is converted into the X-ray energy, for example, preferably, the energy is equal to 1 keV or lower. However, this may significantly increase the measurement frequency, requiring longer time and more effort. In the example, in order to reduce the time and effort required for the measurement, the X-ray photon equal to or higher than the set threshold value is counted to acquire the measured value of the attenuation value.

Figure 8:
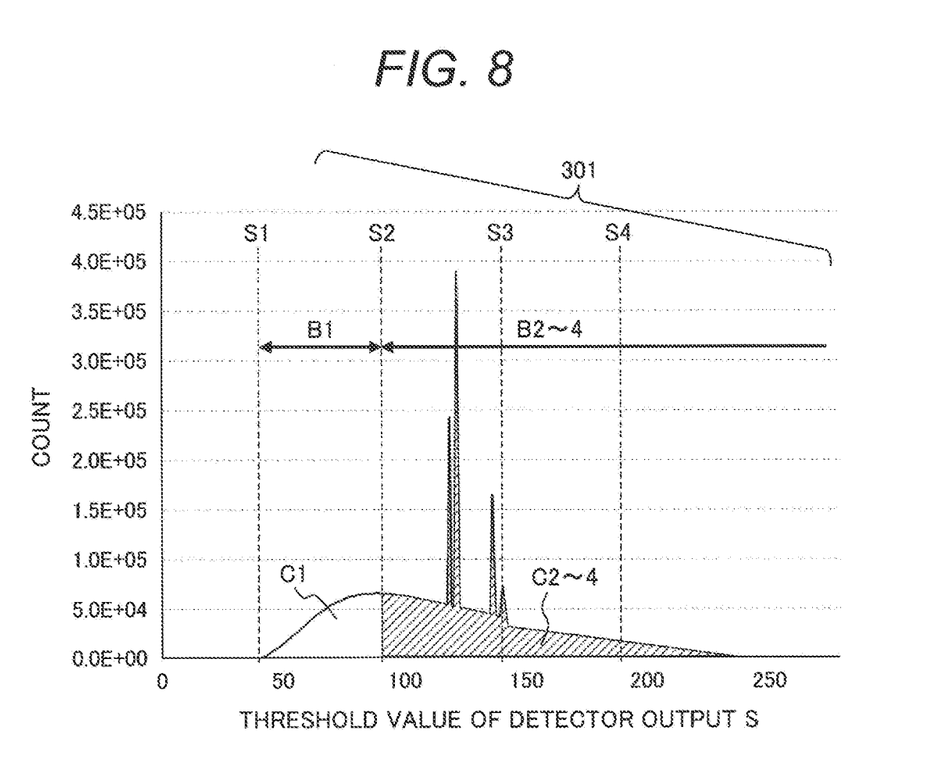
FIG. 8 is a view showing an example of measuring an attenuation value by counting the X-ray photons equal to or higher than the set threshold value.

Referring to FIG. 8, an explanation will be made on the upper addition processing as the processing of measuring the attenuation value by counting the X-ray photons, each of which is equal to or higher than the set threshold value. An x-axis and a y-axis of FIG. 8 denote a threshold value S of the detector output, and the count number of the X-ray photon, respectively. FIG. 8 shows threshold values S1 to S4, in reference to which the X-ray with the energy spectrum 301 is divided into four bins B1 to B4. In the example, the X-ray photon corresponding to the energy equal to or higher than the set threshold value is counted. For example, the count number of the X-ray photons upon setting of the threshold value S2 becomes equivalent to the area of hatched line region from C2 to C4. The count number upon setting of the threshold value S1 becomes equivalent to the total area of the regions C1, and C2 to C4. The use of the result ensures to derive the count number of the bin B1 from the difference in the count number between the case where the threshold value S1 is set and the case where the threshold value S2 is set.

In the upper addition processing, execution of the measurement by setting the single threshold value twice may provide the count numbers of the two bins. Compared with the case of executing the measurement by setting the two threshold values twice, the above-described processing may reduce the time and effort. The attenuation value Am(S) measured in the upper addition processing decreases monotonously relative to the increase in the threshold value S in the range above the photoelectric effect absorption edge of the calibration member. It is therefore possible to easily perform collation between the measured value and the theoretical value of the attenuation value.

The theoretical value calculation unit 452 calculates the theoretical value of the attenuation value in the presence of the calibration member with respect to multiple energies. A theoretical value Ai of the attenuation value is derived from the following formula using an attenuation coefficient p of the calibration member property and a thickness t of the calibration member.

$$Ai = \exp(-\mu \cdot t) \quad \text{(formula 3)}$$

Since the attenuation coefficient p is a function of the energy E, the theoretical value Ai of the attenuation value also becomes the function of the energy E. The formula 3 is rewritten into the following formula to calculate the theoretical value of the attenuation value with respect to multiple energies.

$$Ai(E) = \exp\{-\mu(E) \cdot t\} \quad \text{(formula 4)}$$

It is preferable to correct the thickness t of the calibration member in accordance with the shape of the calibration member to be used. For example, if the flat plate type calibration member 501 is used, the thickness may be corrected in accordance with an incident angle of the X-ray onto the flat plate type calibration member 501. If the arc type calibration member 502 is used, the correction as described above is not required.

The calibration information acquisition unit 453 acquires the relation between the threshold value of the detector output and energy as the calibration information by performing collation between the measured value and the theoretical value of the attenuation value. That is, the correspondence relation between the threshold value S of the detector output and the energy E is obtained so that the measured value Am(S) of the attenuation value as the function of the threshold value S of the detector output is consistent with the theoretical value Ai(E) of the attenuation value as the function of the energy E. The resultant correspondence relation is acquired as the calibration information. That is, the relation between the threshold value S of the detector output and the energy E is not directly handled but acquired indirectly via the measured value and the theoretical value of the attenuation value.

Figure 9:
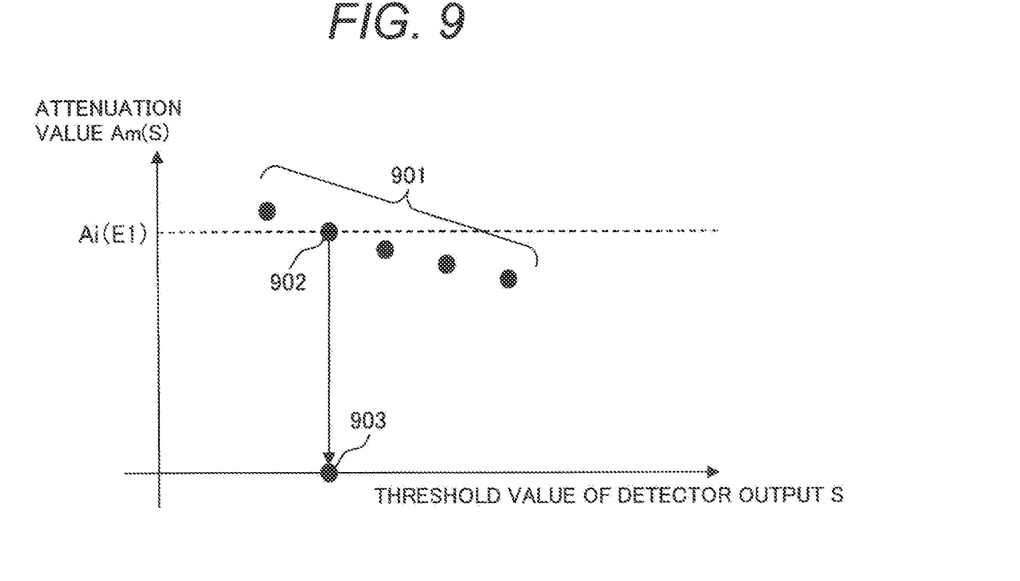
FIG. 9 is a view showing an example of a method of obtaining a correspondence relation between the threshold value of the detector output and energy.

Referring to FIG. 9, an explanation will be made on an example of the method for obtaining the correspondence relation between the threshold value of the detector output and energy via the measured value and the theoretical value of the attenuation value. An x-axis and a y-axis of FIG. 9 denote the threshold value S of the detector output and the measured value Am(S) of the attenuation value, respectively. Using a measured value group 901 of the attenuation values which have been measured while changing the threshold value S of the detector output shown in FIG. 9, the correspondence relation between the threshold value of the detector output and energy is obtained. Firstly, using the (formula 4), the theoretical value Ai(E1) of the attenuation value under the energy E1 of the X-ray photon is calculated based on the material property and the thickness of the calibration member. Then, a measured value 902 of the attenuation value, which is coincided with or the closest to the Ai(E1), is searched from the measured value group 901 of the attenuation value. A threshold value 903 corresponding to the measured value 902 of the attenuation value obtained as the search result is corresponded to the energy E1. The above-described method corresponds the X-ray photon energy to the threshold value of the detector output with respect to each of the detector pixels P so that the correspondence relation is acquired as the calibration information of each of the detector pixels P.

There may be a case where collation between the measured value and the theoretical value of the attenuation value brings about disorder in acquiring the calibration information because the attenuation value becomes discontinuous at the photoelectric effect absorption edge of the calibration member. That is, a plurality of measured values of the attenuation value as the search result are obtained with respect to the theoretical value of the specific attenuation value. This may cause the disorder as to which measured value from the search result is corresponded. As described above, in the case where the absorption edge exists only at the energy side lower than the threshold value of the upper addition processing, the measured attenuation value Am(S) decreases monotonously relative to the increase in the value S. Multiple measured values are not obtained as the search result, and accordingly, the collation between the measured value and the theoretical value of the attenuation value may be easily performed.

Based on the calibration information, the calibration processing unit 454 converts the electric signal outputted from the photon counting type detector into energy. The conversion performed by the calibration processing unit 454 allows the photon counting type detector to perform energy decomposition. It is possible to generate the medical image having the energy divided into a plurality of energy components using the energy decomposition result.

Figure 5:
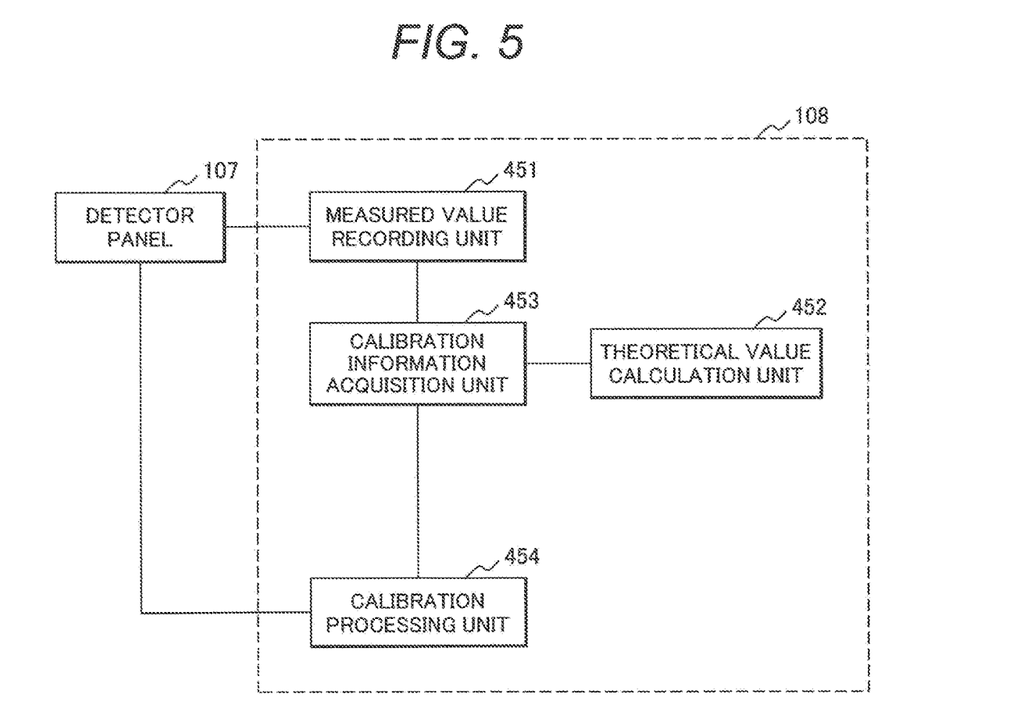
FIG. 5 is an explanatory view of essential parts of Example 1.
Figure 10:
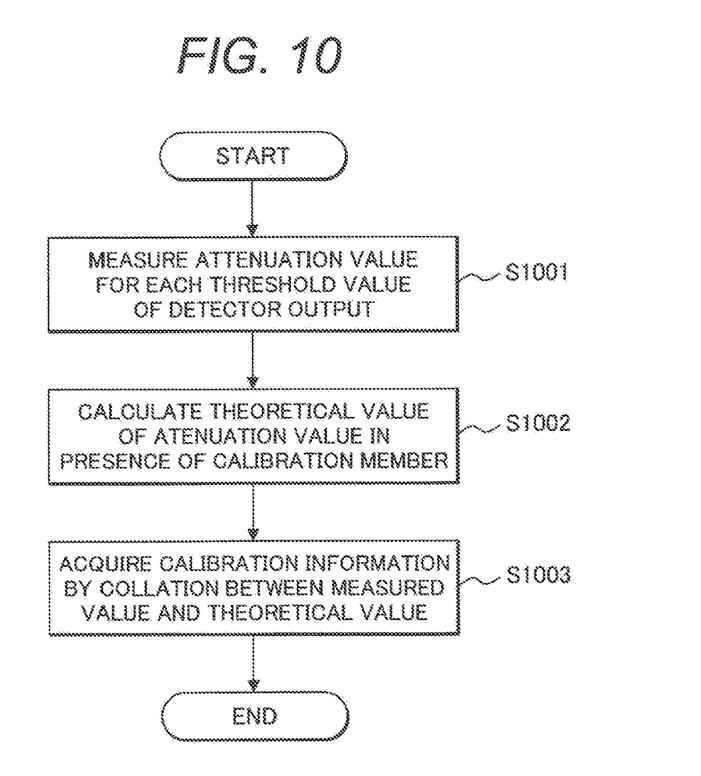
FIG. 10 is a view showing a process flow of acquiring calibration information.

Referring to FIG. 10, the process flow to be executed by the respective units as shown in FIG. 5 will be described.

(S1001)

The measured value recording unit 451 measures the attenuation value for each threshold value of the detection output. Specifically, the count number C of the X-ray photon in the presence of the calibration member, and the count number CO of the X-ray photon in the absence of the calibration member are measured. Based on the measurement results, the measured value of the attenuation value is acquired. The measured value of the attenuation value is recorded with respect to each of the detector pixels P for each threshold value of the detector outputs.

(S1002)

The theoretical value calculation unit 452 calculates the theoretical value of the attenuation value in the presence of the calibration member used for measuring the attenuation value. The theoretical value of the attenuation value is calculated with respect to multiple energies.

(S1003)

The calibration information acquisition unit 453 performs collation between the measured value and the theoretical value of the attenuation value to acquire the relation between the threshold value of the detector output and energy as the calibration information. As described referring to FIG. 9, the measured value of the attenuation value which is coincided with or the closest to the theoretical value of the attenuation value under the specific energy is searched. The threshold value corresponding to the measured value of the attenuation value which has been obtained as the search result is corresponded to the energy used for calculating the theoretical value. Alternatively, the theoretical value of the attenuation value which is coincided with or the closest to the measured value of the attenuation value in reference to the specific threshold value may be searched. The energy corresponding to the theoretical value of the attenuation value which has been obtained as the search result is corresponded to the threshold value used for measuring the attenuation value.

Execution of the process flow as described above may improve accuracy in calibration of the photon counting type detector while ensuring easy and quick calibration.

The radiation imaging apparatus according to the present invention is not limited to the above example, and may be implemented by modifying the components without departing from the scope of the present invention. The plurality of components disclosed in the example may be arbitrarily combined. Furthermore, it is also possible to delete some components from all the components constituting the structure described in the example.

REFERENCE SIGNS LIST

101 . . . X-ray CT apparatus,
102 . . . gantry,
103 . . . X-ray tube,
04 . . . bow tie filter,
105 . . . bed,
106 . . . subject examinee,
107 . . . detector panel,
108 . . . arithmetic unit,
109 . . . input unit,
110 . . . display unit,
201 . . . pulse output,
201L . . . pulse output under low incident energy, 201M . . . pulse output under medium incident energy,
201H . . . pulse output under high incident energy,
301 . . . energy spectrum,
401 . . . energy characteristic expressed by linear equation,
402 . . . energy characteristic (non-linear) of detector pixel P,
451 . . . measured value recording unit,
452 . . . theoretical value calculation unit,
453 . . . calibration information acquisition unit,
454 . . . calibration processing unit,
501 . . . flat plate type calibration member,
502 . . . arc type calibration member,
601 . . . X-ray photon count number in the absence of calibration member,
602 . . . X-ray photon count number in the presence of calibration member,
901 . . . measured value group of attenuation value,
902 . . . measured value of attenuation value which is coincided with or the closest to the theoretical value,
903 . . . threshold value corresponding to energy E1.

What is claimed is:

1. A radiation imaging apparatus provided with a photon counting type detector for outputting an electric signal corresponding to energy of an incident radiation photon, comprising:
    a measured value recording unit for measuring an attenuation value in the presence of a known calibration member while changing a threshold value of a detector output of the photon counting type detector and recording a measured value of the attenuation value for each threshold value of the detector output;
    a theoretical value calculation unit for calculating a theoretical value of the attenuation value in the presence of the calibration member with respect to multiple energies;
    a calibration information acquisition unit for acquiring a relation between the threshold value and the energy as calibration information by performing collation between the measured value and the theoretical value; and
    a calibration processing unit for converting the electric signal outputted from the photon counting type detector into energy based on the calibration information.

2. The radiation imaging apparatus according to claim 1, wherein the measured value recording unit measures the attenuation value in the presence of the calibration member by counting radiation photons equal to or higher than the threshold value of the detector output.

3. The radiation imaging apparatus according to claim 1, wherein the calibration member has a uniform thickness.

4. A calibration method for a photon counting type detector for outputting an electric signal corresponding to energy of an incident radiation photon, the calibration method comprising:
    a measured value recording step of measuring an attenuation value in the presence of a known calibration member while changing a threshold value of a detector output of the photon counting type detector and recording a measured value of the attenuation value for each threshold value of the detector output;
    a theoretical value calculation step of calculating a theoretical value of the attenuation value in the presence of the calibration member with respect to multiple energies; and
    a calibration information acquisition step of acquiring a relation between the threshold value and the energy as calibration information by performing collation between the measured value and the theoretical value.

5. The calibration method for a photon counting type detector according to claim 4,
    wherein in the measured value recording step, the attenuation value in the presence of the calibration member is measured by counting radiation photons equal to or higher than the threshold value of the detector output.

6. The calibration method for a photon counting type detector according to claim 4,
    wherein the calibration member has a uniform thickness.

* * * * *